United States Patent [19]

Fastman

[11] Patent Number: 5,710,536
[45] Date of Patent: Jan. 20, 1998

[54] ADAPTIVE COIL WRAP APPARATUS

[75] Inventor: Gerald E. Fastman, Upper Providence, Pa.

[73] Assignee: Electronic De-Scaling 2000, Inc., Boothwyn, Pa.

[21] Appl. No.: 601,553

[22] Filed: Feb. 14, 1996

[51] Int. Cl.⁶ .................................................. A01F 41/02
[52] U.S. Cl. ........................................................ 336/200
[58] Field of Search ............................... 128/419, 784, 128/799; 29/602.1, 605–606; 336/96–107, 192, 200; 264/272.19

[56] References Cited

U.S. PATENT DOCUMENTS

| | | | |
|---|---|---|---|
| 1,732,937 | 10/1929 | Jones | 336/185 |
| 1,960,033 | 5/1934 | Smith | 175/361 |
| 2,355,477 | 8/1944 | Stahl | 242/119 |
| 3,108,325 | 10/1963 | Harvey et al. | 18/16.5 |
| 3,188,591 | 6/1965 | Dortort | 336/185 |
| 3,195,335 | 7/1965 | Brower et al. | 72/56 |
| 3,278,877 | 10/1966 | Kameya | 336/136 |
| 3,321,946 | 5/1967 | Ferguson | 72/56 |
| 3,347,074 | 10/1967 | Eilers et al. | 72/56 |
| 3,391,558 | 7/1968 | Deeg | 72/56 |
| 3,423,978 | 1/1969 | Kline | 72/56 |
| 3,486,356 | 12/1969 | Brower et al. | 72/56 |
| 3,507,034 | 4/1970 | Schwinghamer et al. | 29/517 |
| 3,544,940 | 12/1970 | Davis | 336/192 |
| 3,602,023 | 8/1971 | Furth | 72/56 |
| 3,605,055 | 9/1971 | Grady | 336/185 |
| 3,654,787 | 4/1972 | Brower | 72/56 |
| 3,661,342 | 5/1972 | Sears | 242/118.41 |
| 3,689,862 | 9/1972 | Hilgers | 336/206 |
| 3,810,373 | 5/1974 | Queyoix | 72/56 |
| 3,893,462 | 7/1975 | Manning | 128/421 |
| 4,039,924 | 8/1977 | Scales et al. | 363/65 |
| 4,066,065 | 1/1978 | Kraus | 128/1.5 |
| 4,105,017 | 8/1978 | Ryaby et al. | 128/1.5 |
| 4,266,532 | 5/1981 | Ryaby et al. | 128/1.5 |
| 4,266,533 | 5/1981 | Ryaby et al. | 128/1.5 |
| 4,313,438 | 2/1982 | Greatbatch | 128/207.21 |
| 4,315,503 | 2/1982 | Ryaby et al. | 128/1.5 |
| 4,421,115 | 12/1983 | Kraus | 128/419 F |
| 4,442,331 | 4/1984 | Watanabe | 219/10.43 |
| 4,456,001 | 6/1984 | Pescatore | 128/1.5 |
| 4,459,988 | 7/1984 | Dugot | 128/420 R |
| 4,467,808 | 8/1984 | Brighton et al. | 128/419 R |
| 4,467,809 | 8/1984 | Brighton | 128/419 R |
| 4,501,265 | 2/1985 | Pescatore | 128/1.5 |
| 4,514,712 | 4/1985 | McDougal | 336/96 |
| 4,519,394 | 5/1985 | Black et al. | 128/419 F |
| 4,520,360 | 5/1985 | Schwab | 340/947 |
| 4,527,550 | 7/1985 | Ruggera | 128/1.5 |
| 4,531,393 | 7/1985 | Weir | 72/56 |
| 4,535,775 | 8/1985 | Brighton et al. | 128/419 F |

(List continued on next page.)

FOREIGN PATENT DOCUMENTS

| | | | |
|---|---|---|---|
| 525936 | 2/1954 | France. | |
| 2309023 | 11/1976 | France | H01F 27/28 |
| 2326769 | 4/1977 | France | H01F 5/02 |
| 278842 | 10/1927 | United Kingdom . | |

*Primary Examiner*—Aditya Krishnan
*Attorney, Agent, or Firm*—Robert S. Lipton, Esq.; Lipton, Weinberger & Husick

[57] ABSTRACT

A solenoid coil includes a substantially parallel plurality of conductors on a flexible base. The flexible base is wound around a water pipe, body part or the like to provide a field for the treatment of fluids therein. An alignment mechanism is provided to substantially align a first level of parallel conductors to the next level of parallel conductors above the first level. Each wrap of the flexible base provides a number of conductor turns equal to the number of parallel conductors. In a second embodiment, a substantially parallel first plurality of conductors and a substantially parallel second plurality of conductors are disposed on a flexible base. A return conductor is provided on the flexible base to connect the first plurality of conductors to the second plurality of conductors. When wound around a fluid carrying pipe, the return conductor is disposed up flow (i.e., upstream) from the first and second plurality of conductors, so as to prevent destructive interference with the desired additive field within the pipe.

8 Claims, 6 Drawing Sheets

U.S. PATENT DOCUMENTS

| | | | |
|---|---|---|---|
| 4,548,208 | 10/1985 | Niemi | 128/419 F |
| 4,549,547 | 10/1985 | Brighton et al. | 128/419 F |
| 4,550,714 | 11/1985 | Talish et al. | 128/1.5 |
| 4,556,051 | 12/1985 | Maurer | 128/1.5 |
| 4,561,426 | 12/1985 | Stewart | 128/1.5 |
| 4,672,951 | 6/1987 | Welch | 128/1.5 |
| 4,674,482 | 6/1987 | Waltonen et al. | 128/1.5 |
| 4,701,830 | 10/1987 | Kato et al. | 361/395 |
| 4,757,804 | 7/1988 | Griffith et al. | 128/1.5 |
| 4,759,120 | 7/1988 | Bernstein | 29/605 |
| 4,837,544 | 6/1989 | McDougal | 336/185 |
| 4,888,571 | 12/1989 | Kobayashi | 336/65 |
| 4,985,984 | 1/1991 | Umezaki | 29/602.1 |
| 4,993,313 | 2/1991 | McLeod et al. | 128/419 |
| 5,162,769 | 11/1992 | Dolan et al. | 335/299 |
| 5,208,573 | 5/1993 | Nagaoka | 336/192 |
| 5,373,276 | 12/1994 | Suppelsa et al. | 336/65 |

ADAPTIVE COIL WRAP APPARATUS

FIELD OF THE INVENTION

This invention relates to an improvement in the field of coils, as for example the solenoid coil used for electronic descaling wherein fluids are treated by exposure to magnetic and electric fields.

BACKGROUND OF THE INVENTION

Coils for generating electric and magnetic fields are useful in many applications. For example, problems caused by hard water such as scale deposits of dissolved minerals on the interior surfaces of pipes, are treated by exposing hard water to magnetic fields. An energized solenoid cable wrapped around a pipe for the purpose of treating fluids within the pipe with electrical and magnetic fields is known from U.S. Pat. Nos. 5,074,998, 5,171,431, 4,326,954, 2,596,743 and 3,843,507.

Any of the above cited patents show an energized coil wrapped around a pipe for the purpose of exposing fluids within the pipe to electric and magnetic fields. Solenoid coils are also useful in other fields, such the automotive field to generate linear motion to engage the electric starter to the gasoline engine.

Solenoid coils are further useful in the medical field to treat blood or living tissue. In U.S. Pat. No. 4,993,413 a coil is shown consisting of a multi-conductor ribbon cable with offset connectors to form an inductor.

One problem in the use of solenoid coils in many applications is the installation, removal and replacement of the coil itself. For example, in fluid treatment applications, the coil is typically installed around an existing water pipe. It is usually not practical to disconnect the water pipe and slip a prewound coil over the pipe. Also, since pipes come in many diameters, a prewound coil would have to be matched to the pipe. As a result, previously known coils are wound around the pipe one turn at a time, which can be a laborious and burdensome process especially for a large number of turns. Thus, it would be desirable to provide a solenoid coil adaptable to various sizes of existing pipes, and be installed quickly, accurately and easily.

SUMMARY OF THE INVENTION

The present invention is embodied in a solenoid coil comprising a substantially parallel plurality of conductors on a flexible base. First ends of each of the plurality of conductors are connected together. Second ends of each of the plurality of conductors are connected together. The flexible base is wound around a water pipe, bodypart or the like. An alignment mechanism is provided to substantially align a first level of parallel conductors to the next level of parallel conductors above the first level. The first level need not be directly on top of the lower level, but the two levels can be offset, so long as the alignment provides a fixed relationship between conductors on the first and second levels. An input terminal is coupled to one end of each of the plurality conductors, while an output terminal is coupled to the other end of each of the substantially plurality conductors. A coil is thus formed around the pipe.

In operation, a power supply is coupled to the input terminal and the output terminal to provide current through each of the parallel conductors. Each wrap of the flexible base provides a number of conductor turns equal to the number of parallel conductors. The substantial alignment each of the parallel conductors with the corresponding conductor above and below, carries current in the same direction around the pipe. As a result, the magnetic and electric fields generated are additive to produce a desired field within the water pipe.

In a second embodiment of the present invention, a substantially parallel first plurality of conductors and a substantially parallel second plurality of conductors are disposed on a flexible base. First ends of the first plurality of conductors are connected together and coupled to a first terminal of said first plurality of conductors. First ends of the second plurality of conductors are connected together and coupled to a first terminal of said second plurality of conductors. Second ends of the first plurality of conductors are connected together and coupled to a second terminal of said first plurality of conductors. Second ends of the second plurality of conductors are connected together and coupled to a second terminal of said second plurality of conductors.

A return conductor is provided on the flexible base to connect the second terminal of said first plurality of conductors to the first terminal of said second plurality of conductors. An input terminal is coupled to the first terminal of said first plurality conductors, while an output terminal is coupled to the second terminal of said second plurality of conductors. A coil is thus formed around the pipe.

In operation, a power supply is coupled to the input terminal and the output terminal to provide current through each of the first plurality of conductors, and, via the return conductor, through each of the second plurality of conductors. Each wrap of the flexible base provides a number of conductor turns equal to the number of parallel conductors. Also, the substantial alignment each of the conductors with its own corresponding respective conductor above and below the current turn around the pipe, provides a collinear unidirectional current carried in the same direction around the pipe. As a result, the magnetic and electric fields generated are additive to produce a desired field within the water pipe.

The return conductor provides a reverse field relative to the additive field generated by the first plurality of parallel conductors and the second plurality of parallel conductors. In accordance with another aspect of the present invention, the return conductor is disposed up flow (i.e., upstream) from the first and second plurality of conductors. Since the return conductors are placed upstream from the first plurality of conductors, destructive interference with the desired additive field within the water pipe is prevented.

Thus, a coil formed with the adaptive coil apparatus of the present invention requires fewer hand turns to form, since multiple conductors are wrapped at the same time. When formed, the adaptive coil apparatus will conform to the pipe diameter, and have the proper spacing between the individual wires and successive layers. In addition, the flexible base and alignment device assures that coil will fit pipes of any diameter.

DETAILED DESCRIPTION

Figure 1:
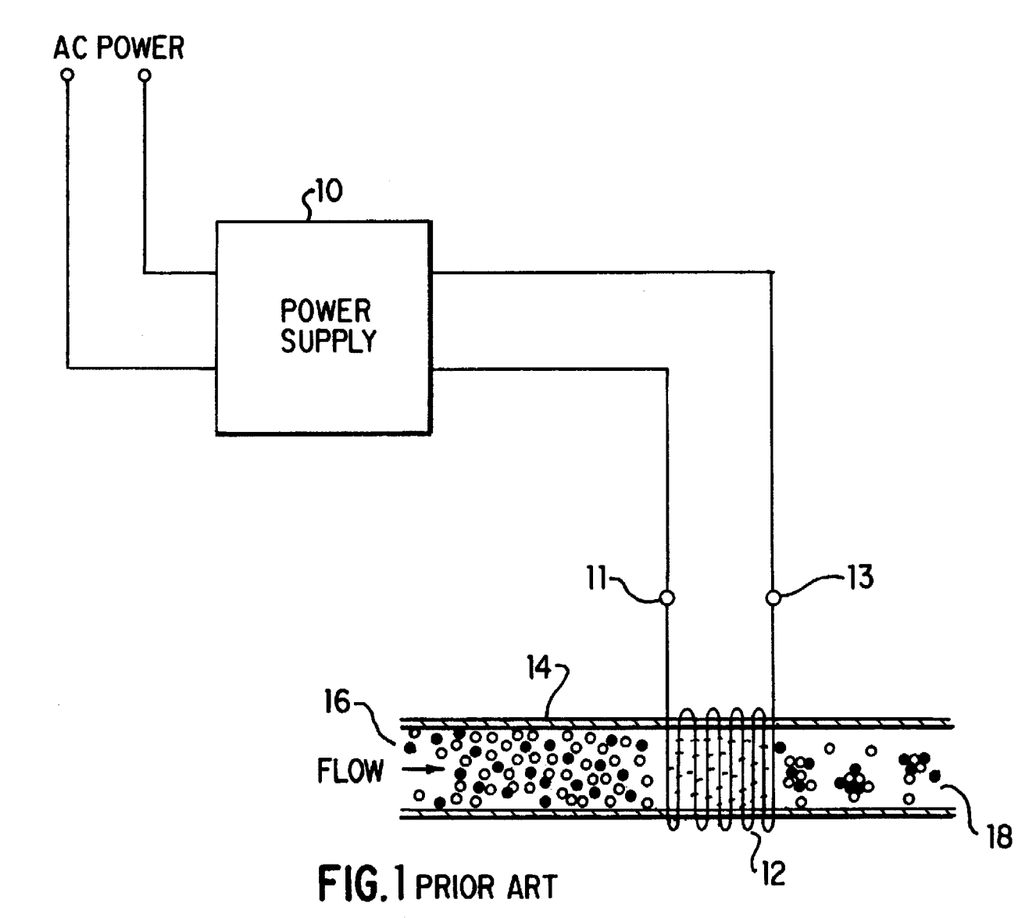
FIG. 1 is a block diagram of a system embodying a solenoid coil in accordance with the prior art for used in an electronic descaling system.

A conventional coil, or solenoid as for use in an electronic water treatment apparatus, is shown in FIG. 1. Coil 12 is wrapped around a water pipe 14. A power supply 10, coupled to the AC line, provides appropriate current to the coil. The field generated by the coil 12 inside the pipe 14 treats input water flow 16 to affect electronic descaling in the output water flow 18.

Typically, coil 12 is installed around an existing water pipe. Accordingly, coil 12 is installed by hand, wrapping it one turn at a time around pipe 14, and connecting power supply 10 via terminals 11 and 13. To remove the coil 12, the power supply 10 is disconnected at terminals 11 and 13, and the coil 12 unwrapped one turn at a time by hand.

Figure 2:
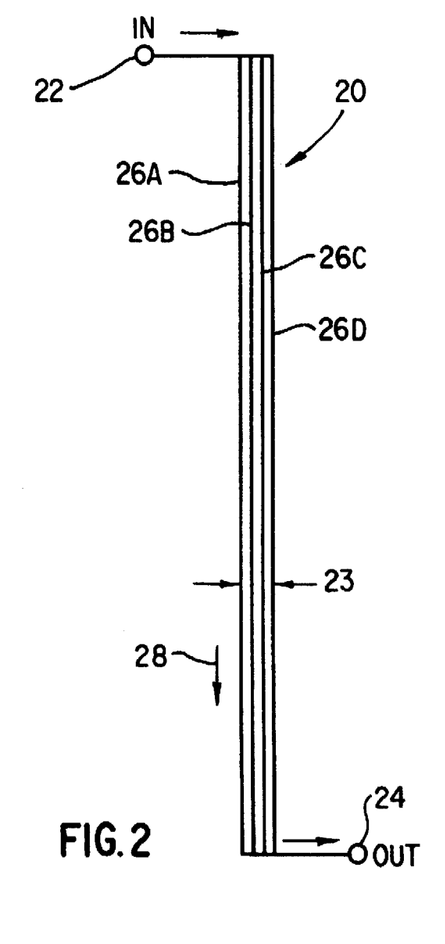
FIG. 2 is an illustration of a flexible circuit for forming a coil, in accordance with the present invention.

A coil wrap apparatus 20 in accordance with the present invention is shown in FIG. 2. A plurality of parallel conductors 26A, 26B, 26C and 26B are coupled between input terminal 22 and output terminal 24. The parallel conductors 26A, 26B, 26C and 26B are formed on or within a flexible base (reference numeral 30 in FIG. 4), such as for example, a plastic sheet material of the type used for flexible printed circuits. The flexible base may also be the insulation of a ribbon cable of the type used to encapsulate wires for interconnections in electronic equipment.

Figure 3:
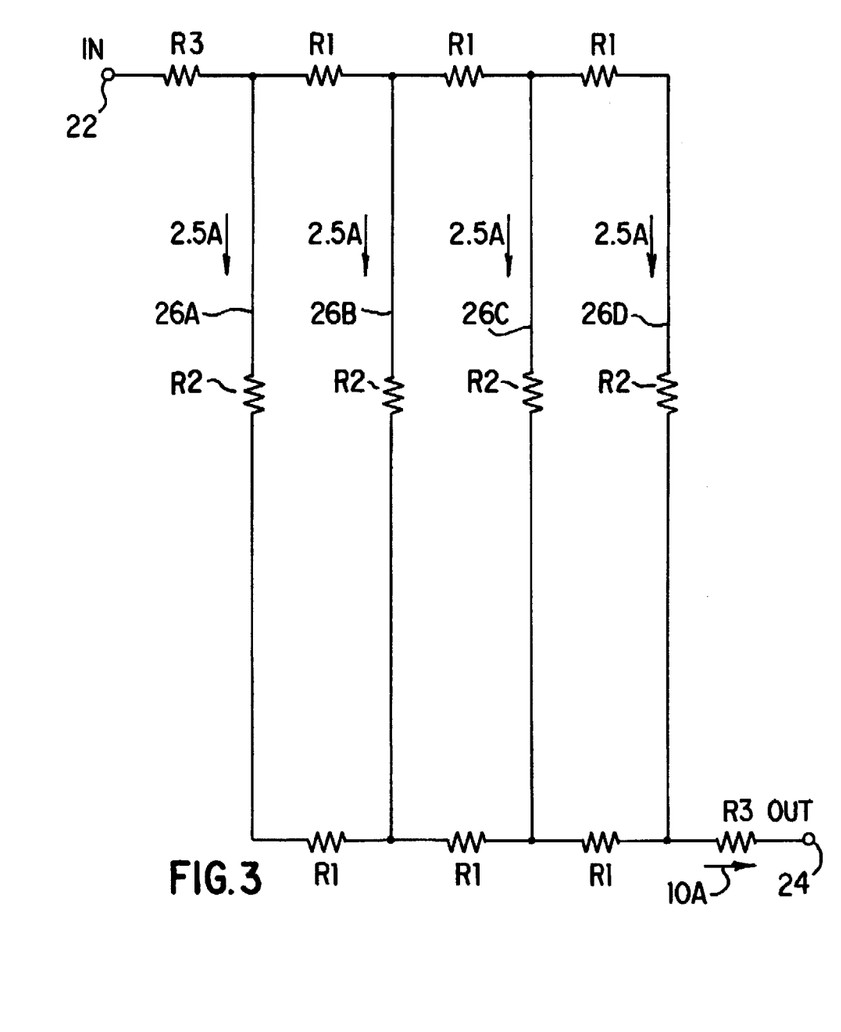
FIG. 3 is a schematic diagram of a flexible circuit for forming a coil, in accordance with the present invention.

A schematic diagram of the coil wrap apparatus 20 is shown in FIG. 3. Each of the parallel conductors 26A, 26B, 26C and 26B is represented by a resistor R1. The coupling between parallel conductors is represented by a resistor R1, and the coupling between the parallel conductors to the input terminal, and to output terminal, respectively by a respective resistor R3.

The coil wrap apparatus 20 is preferably symmetrical between input and output so that the total impedance between the input terminal 22 and the output terminal 24 through each respective parallel conductor 26A, 26B, 26C and 26B should be equal. If so, the input current between terminal 22 and 24 is more or less equally divided.

For example, in FIG. 3 the resistive impedance through parallel conductor 26A (ignoring the other parallel conductors) from input terminal 22 to output terminal 24 is 2R3+3R1+R2. Similarly, the resistive impedance from input to output through conductor 26B is the same, as is the resistive impedance from input to output through conductors 26C and 26D. Accordingly, an input current of 10 amperes will be approximately equally divided into 2.5 amperes in each of parallel conductors 26A, 26B, 26C and 26B. An alternative to symmetrical construction is to trim a portion of the width of each parallel conductor in the manufacturing process so as to control the total path resistance. For this purpose, the lower resistance paths may be increased by laser trimming a portion of each path at a site on the flexible base provided for this purpose.

Figure 4:
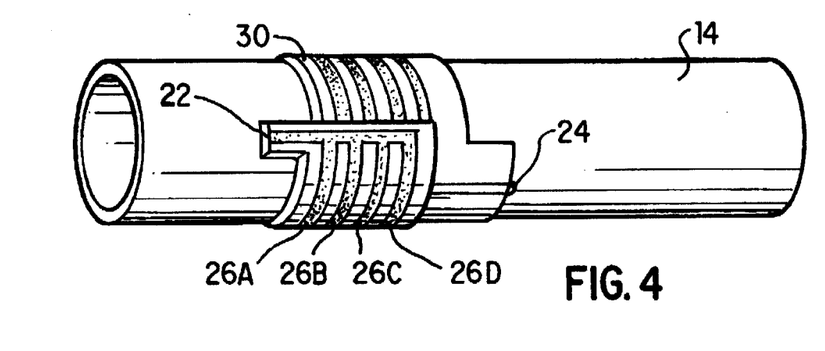
FIG. 4 is an isometric view of a coil forming apparatus positioned around a support in accordance with the present invention.
Figure 5:
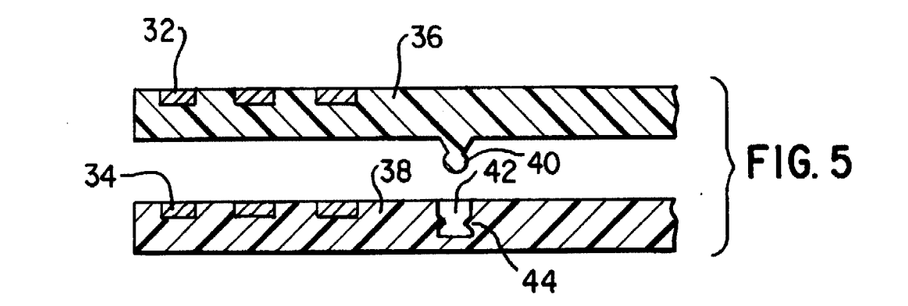
FIG. 5 is a crossectional view of an alignment device for use in conjunction with the present invention.
Figure 6:
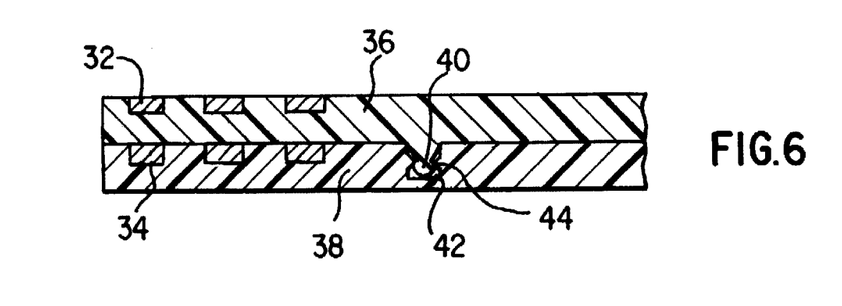
FIG. 6 is crossectional view of an alignment device positioned to align conductors for use in conjunction with the present invention.

The coil wrap apparatus is shown installed around a pipe 14 in FIG. 4. The flexible base 30 is bent to conform to the surface of pipe 14. Successive turns around the pipe are layered to align the conductors 26A, 26B, 26C and 26D over prior turns. An device to achieve alignment between successive turns is shown in FIG. 5 and 6.

Conductor 32 and 34 are successive turns of the same one of the parallel conductors, as is base 36 and 38 successive turns of the same flexible base. Alignment is effected by protrusion 40 on the bottom surface of the flexible base 30, and a recess 42 on the top surface of the flexible base 30. Both the protrusion 40 and recess 42 are longitudinal formations along the entire length of flexible base 30. The linear alignment device shown may be used with any diameter pipe.

When protrusion 40 seats into recess 42, the conductors 32 and 34 are aligned vertically with respect to one another. Internal ridges 44 in the recess 42 act to retain protrusion 40 in recess 42, and to provide a positive sound and feel when proper alignment is achieved.

Figure 7:
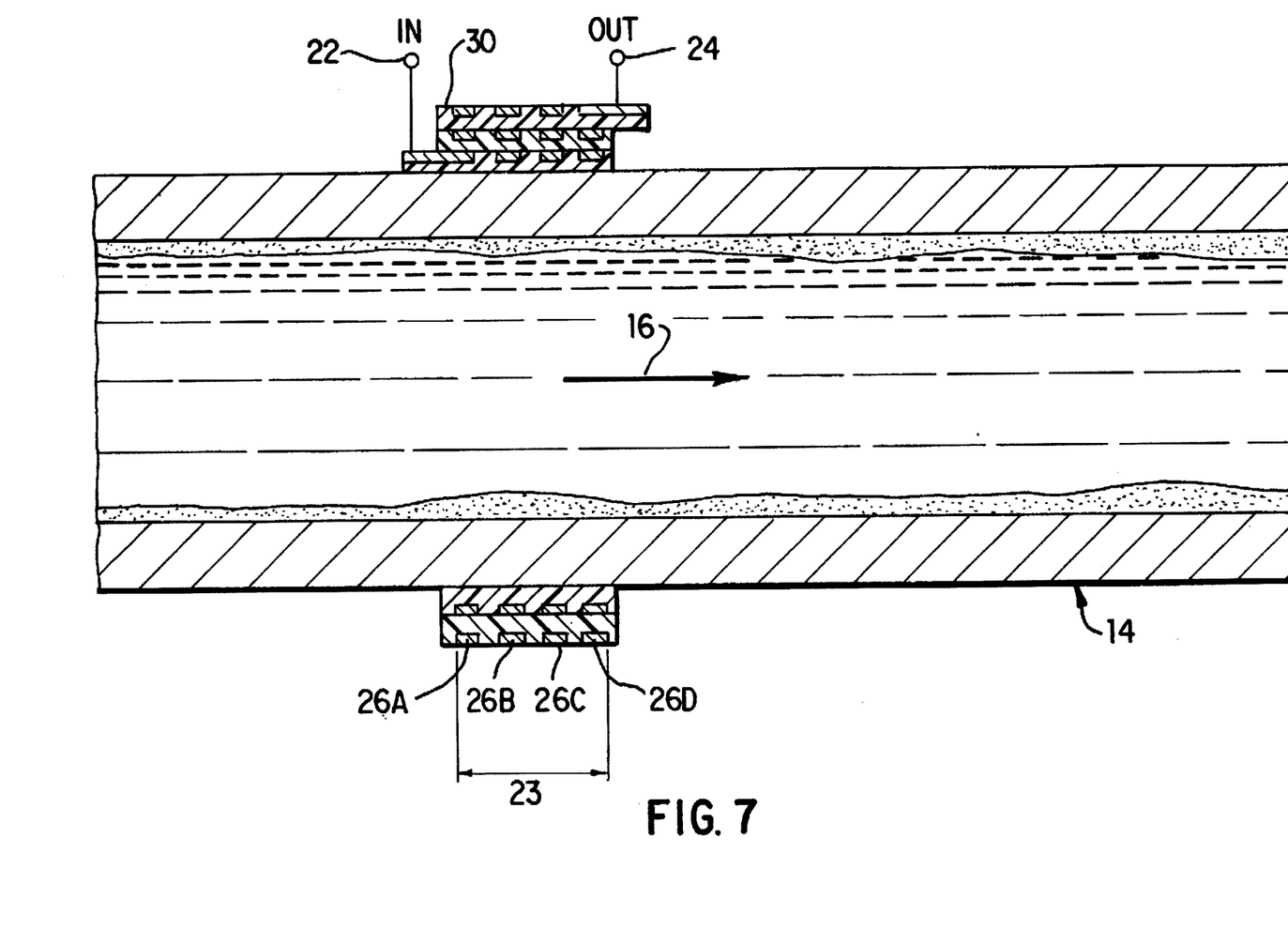
FIG. 7 is crossectional view of a fluid carrying pipe and a coil forming apparatus in accordance with the present invention.

A crossectional view of coil 20 installed on a water pipe 14 is shown in FIG. 7. Flexible base 30 provides two complete turns around the pipe. The first turn of conductors 26A, 26B, 26C and 26D are aligned with respect to the second turn of the respective conductors. The active area of the coil is region 23 between the conductors 26A and 26D at the extremities of adaptive coil wrap apparatus. An energizing current between input terminal 22 and output terminal 24 provides a field within pipe 14.

Thus, with each successive wrap of the adaptive coil wrap apparatus, 4 conductors are wrapped at the same time. In addition, the flexible base and alignment device assures that a coil will be properly formed, with proper spacing between the individual wires and layers.

It is noted that the current in each of the parallel conductor is added to determine the total current requirement of the power supply. For a large number of parallel conductors, the current requirement increases. In order to reduce the amount of current required from the power supply, a second embodiment using more than one parallel plurality of conductors and current return conductors is shown in FIG. 8.

Figure 8:
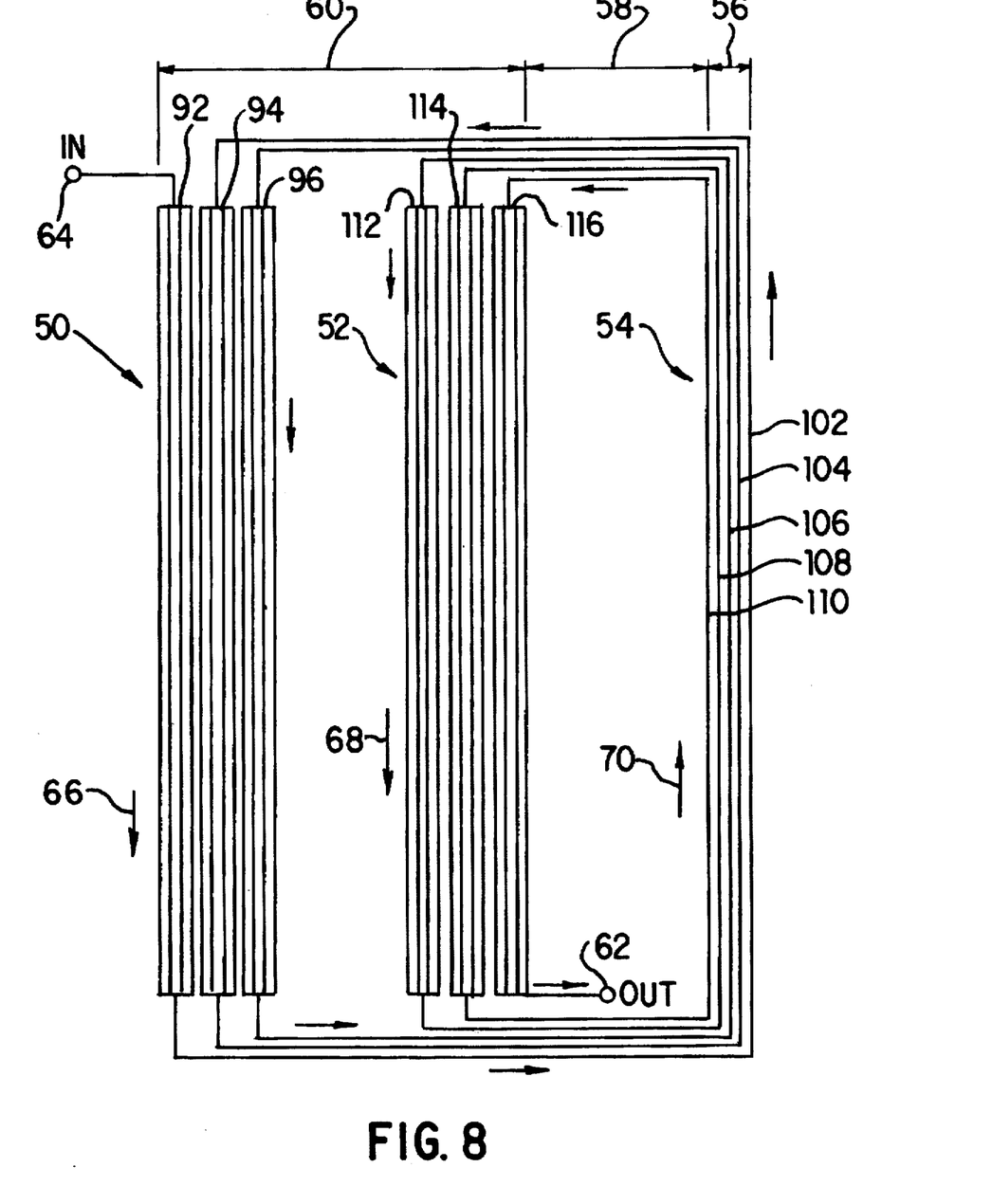
FIG. 8 is an illustration of a flexible circuit for forming a coil, in accordance with a second embodiment of the present invention.

An adaptive coil wrap apparatus in FIG. 8 has 24 parallel conductors and 5 current return conductors. The 24 parallel conductors are divided into 6 groups of 4 parallel conductors each. Three of the groups 50 consist of 3 sub-groups 92, 94 and 96. The other three groups 52 consist of 3 sub-groups 112, 114 and 116. Each of the sub-groups 92, 94, 96, 112, 114 and 116 consist of 4 substantially parallel conductors. The current return conductors 102, 104, 106, 108 and 110 connect the 6 groups in series between the input terminal 64 and the output terminal 62.

In particular, the first set of parallel conductors 92 are connected together at one end and coupled to input terminal 64. The other ends of parallel conductors 92 are connected together and coupled to current return conductor 102. A second set of parallel conductors 94 are connected together at one end and coupled to the other end of return conductor 102. The other ends of parallel conductors 94 are connected together and coupled to current return conductor 104.

The third set of parallel conductors 96 are connected together at one end and coupled to the other end of return conductor 104. The other ends of parallel conductors 96 are connected together and coupled to current return conductor 106. A fourth set of parallel conductors 112 are connected together at one end and coupled to the other end of return conductor 106. The other ends of parallel conductors 112 are connected together and coupled to current return conductor 108.

The fifth set of parallel conductors 114 are connected together at one end and coupled to the other end of return conductor 108. The other ends of parallel conductors 114 are connected together and coupled to current return conductor 110. A sixth set of parallel conductors 116 are connected together at one end and coupled to the other end of return conductor 110. The other ends of parallel conductors 116 are connected together and coupled to output terminal 62.

The groups of parallel conductors 50, 52 and current return conductors 54 are formed on a flexible base with an alignment device. The coil is installed by wrapping successive turns around a support. Each successive layer has 24 conductors which are aligned with respect to the previous layer of the same 24 conductors to form the coil. Alignment may be directly over a prior turn, or offset slightly.

In operation, the input current at terminal 64 is divided equally between the 4 substantially parallel conductors of the sub-group 92. The current through the parallel conductors of sub-group 92 is carried by current return conductor 102 to the sub-group 94 and so on, through each of the sub-groups in series to the last current return conductor 110 to sub-group 116 to output terminal 62. The total coil current 66 in one group 50 plus the total coil current 68 in the other group 52 equals the total return current 70 in the current return conductor 54. The region 60 is the active area of the coil forming a main field. The region 56 forms the area where the return current 70 forms a reverse field separated from the main field by a gap 58. The gap 58 is provided to separate the reverse field in region 56 from the main field in region 60.

Figure 9:
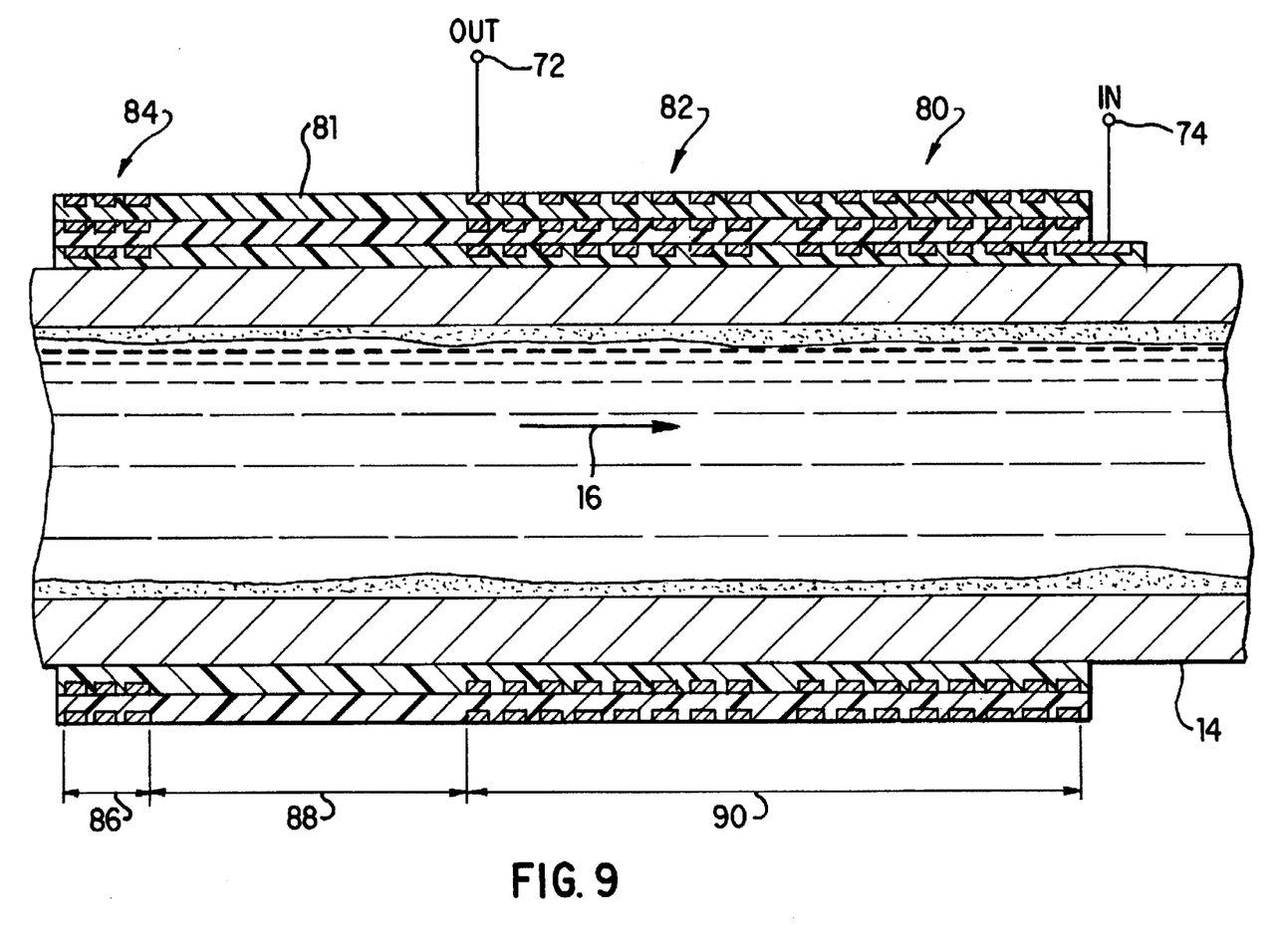
FIG. 9 is crossectional view of a fluid carrying pipe and a coil forming apparatus in accordance with a second embodiment of the present invention.

A crossectional view of an adaptive coil wrap apparatus is shown in FIG. 9. The coil is installed on a water pipe 14. The main section of the coil has two groups 80, 82, each group having sub-groups, each sub-group having 4 substantially parallel conductors. The coil consists of 4 sub-groups which total 16 conductors, plus the 3 current return conductors 84. In general, the number of current return conductors will be one less (N−1) than the number (N) of sub-groups of parallel conductors.

In operation, an energizing current between input terminal 72 and output terminal 74 provides a field within pipe 14. The active area of the coil is region 90 between the conductors at the extremities of adaptive coil wrap apparatus.

The current in the return conductors 84 provides a reverse field in the region 86. In order to avoid the reverse field causing a destructive interference with the descaling effect provided by the main coil in region 90, a gap 88 is provided between the reverse field region 86 and the main field region 90. In addition, the reverse field region 86 is positioned up flow (i.e., upstream) from the conductors in region 90, so as to prevent destructive interference with the desired additive field within the water pipe. The further up stream that region 86 is positioned, the less the destructive interference with main coil region 90. However, the total coil resistance increases as the gap 88 increases. As a compromise between these competing parameters, the gap 88 from the main coil region 90 may be made equal to or larger than the width of the reverse field region 86.

To install the adaptive coil wrap, flexible base 81 is wound around the pipe 14. Two complete turns are shown but it will be appreciated that more turns are contemplated. With each successive wrap of the adaptive coil wrap apparatus, 16 conductors are wrapped at the same time. Each respective turn is aligned with the previous turn as previously indicated. The flexible base 81 and the alignment device assures that a coil will be properly formed on the pipe 14, with proper spacing between the individual wires and layers.

What is claimed is:

1. A coil forming apparatus comprising:

a flexible base;

a substantially parallel plurality of conductors disposed on said flexible base, each of said plurality of conductors having a first terminal and a second terminal;

an input terminal connected to said first terminals of said plurality of conductors;

an output terminal connected to said second terminals of said plurality of conductors;

a support;

said flexible base containing said plurality of conductors being flexed to wrap around said support;

said plurality of conductors on said flexible base being wrapped around said support by more than one complete first turn and at least a portion of a second turn; and an alignment device for aligning one of said plurality of conductors on said second turn with said one of said plurality of conductors on said first turn.

2. An apparatus in accordance with claim 1, wherein said support is a fluid carrying pipe or body part, and further comprising: a power supply having first and second terminals, wherein said input terminal is connected to said first terminal of said power supply, and said output terminal is connected to said second terminal of said power supply.

3. A coil forming apparatus comprising:

a flexible base;

a substantially parallel first plurality of conductors disposed on said flexible base, each of said first plurality of conductors having a first terminal and a second terminal;

a substantially parallel second plurality of conductors disposed on said flexible base, each of said second plurality of conductors having a first terminal and a second terminal;

an input terminal connected to said first terminals of said first plurality of conductors;

an output terminal connected to said second terminals of said second plurality of conductors;

a return conductor connected between said second terminals of said first plurality of conductors and said first terminals of said second plurality of conductors;

a support;

said flexible base containing said first plurality of conductors and said second plurality of conductors being flexed to wrap around said support, said first and second plurality of conductors on said flexible base being wrapped around said support by more than one complete first turn and at least a portion of a second turn; and an alignment device for aligning one of said first plurality of conductors on said second turn with said one of said first plurality of conductors on said first turn, said alignment device further aligning one of said second plurality of conductors on said second turn with said one of said second plurality of conductors on said first turn.

4. A coil forming apparatus in accordance with claim 3, wherein said alignment device comprises:

a protrusion on one side of said flexible base; and a recess on the opposite side of said flexible base, wherein said protrusion is disposed within said recess.

5. A coil forming apparatus comprising:

a flexible base;

a substantially parallel first plurality of conductors disposed on said flexible base, each of said first plurality of conductors having a first terminal and a second terminal;

a substantially parallel second plurality of conductors disposed on said flexible base, each of said second plurality of conductors having a first terminal and a second terminal;

an input terminal connected to said first terminals of said first plurality of conductors;

an output terminal connected to said second terminals of said second plurality of conductors;

a return conductor connected between said second terminals of said first plurality of conductors and said first terminals of said second plurality of conductors; and a support, said flexible base containing said first plurality of conductors and said second plurality of conductors being flexed to wrap around said support, said support being a fluid carrying pipe or body part.

6. An apparatus in accordance with claim 5, further comprising:

a power supply having first and second terminals, wherein said input terminal is connected to said first terminal of said power supply, and said output terminal is connected to said second terminal of said power supply.

7. A coil forming apparatus in accordance with claim 5, wherein said support is a fluid carrying pipe, and said return conductor is disposed at an up flow position along said fluid carrying pipe relative to a down flow position of said first and second plurality of conductors.

8. A coil forming apparatus comprising:

a flexible base;

a substantially parallel first plurality of conductors disposed on said flexible base, each of said first plurality of conductors having a first terminal and a second terminal;

a substantially parallel second plurality of conductors disposed on said flexible base, each of said second plurality of conductors having a first terminal and a second terminal;

an input terminal connected to said first terminals of said first plurality of conductors;

an output terminal connected to said second terminals of said second plurality of conductors;

a return conductor connected between said second terminals of said first plurality of conductors and said first terminals of said second plurality of conductors;

N groups of substantially parallel pluralities of conductors disposed on said flexible base, each of said plurality of conductors having respective first and second terminals; and N-1 return conductors, each of said return conductors connected between one of said second terminals of said first plurality of conductors and one of said first terminals of said second plurality of conductors.

* * * * *